United States Patent
Liu et al.

(10) Patent No.: US 12,031,011 B2
(45) Date of Patent: Jul. 9, 2024

(54) POLYDOPAMINE FILM AND PREPARATION METHOD AND APPLICATION THEREOF

(71) Applicant: B. J. ZH. F. PANTHER MEDICAL EQUIPMENT CO., LTD., Beijing (CN)

(72) Inventors: Qing Liu, Beijing (CN); Cong Pu, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 765 days.

(21) Appl. No.: 16/930,041

(22) Filed: Jul. 15, 2020

(65) Prior Publication Data

US 2021/0054172 A1 Feb. 25, 2021

(30) Foreign Application Priority Data

Aug. 20, 2019 (CN) .......................... 201910766453.8

(51) Int. Cl.
*A61L 31/10* (2006.01)
*A61B 17/11* (2006.01)
(Continued)

(52) U.S. Cl.
CPC ............ *C08K 5/3462* (2013.01); *A61B 17/11* (2013.01); *A61L 31/10* (2013.01); *A61L 31/16* (2013.01);
(Continued)

(58) Field of Classification Search
CPC .......................... A61L 31/10; A61L 2300/404
See application file for complete search history.

(56) References Cited

U.S. PATENT DOCUMENTS

| 4,581,028 | A | * | 4/1986 | Fox, Jr. | ................... | A61B 17/34 |
| | | | | | | 514/157 |
| 4,933,178 | A | * | 6/1990 | Capelli | ................... | A61L 29/16 |
| | | | | | | 424/617 |

(Continued)

FOREIGN PATENT DOCUMENTS

| CN | 104357814 A | 2/2015 | |
| CN | 105431181 A * | 3/2016 | ........... A61L 29/085 |

(Continued)

OTHER PUBLICATIONS

Gao et al. "Antibacterial activity and osseointegration of silver-coated poly(ether ether ketone) prepared using the polydopaime—assisted deposition technique" Journal of Materials Chemistry B; vol. 5, No. 47, Jan. 2017 (Year: 2017).*

(Continued)

*Primary Examiner* — Cachet I Proctor
(74) *Attorney, Agent, or Firm* — HAUPTMAN HAM, LLP

(57) ABSTRACT

Disclosed are a poly dopamine film and a preparation method and application thereof. The polydopamine film is loaded with silver sulfadiazine, and the preparation method achieves in-situ synthesis of si sulfadiazine on a conventional polydopamine film by microwave irradiation. In the method, the sulfadiazine is not dissolved in conventional aqueous ammonia, which has the following advantages: firstly, preventing the polydopamine film from being corroded by the aqueous ammonia; secondly, protecting mucosa such as eyes and nasal cavities of workers from stimulation and corrosion of the aqueous ammonia; and thirdly, avoiding the environmental problem caused by pungent odor and fumes emitted from high-concentration aqueous ammonia. In the method, without using the catalyst trifluoromethanesulfonic acid or trifluoromethanesulfonic (Continued)

salt, not only is the loading of silver sulfadiazine increased, but also the safely performance can be further improved.

1 Claim, 6 Drawing Sheets

(51) Int. Cl.
  A61L 31/16 (2006.01)
  B05D 1/18 (2006.01)
  B05D 3/06 (2006.01)
  C08J 5/18 (2006.01)
  C08K 5/3462 (2006.01)
  A61B 17/00 (2006.01)
  A61B 17/064 (2006.01)
(52) U.S. Cl.
  CPC .......... B05D 1/18 (2013.01); B05D 3/06 (2013.01); C08J 5/18 (2013.01); A61B 2017/00893 (2013.01); A61B 2017/0647 (2013.01); A61L 2300/104 (2013.01); A61L 2300/404 (2013.01); A61L 2420/02 (2013.01); C08J 2379/02 (2013.01)

(56) References Cited

U.S. PATENT DOCUMENTS

| 2007/0003603 | A1* | 1/2007 | Karandikar ......... C23C 18/1646 424/443 |
| 2010/0059433 | A1* | 3/2010 | Freeman ................ B01D 71/60 427/244 |
| 2010/0247544 | A1* | 9/2010 | Vachon ................ A61K 31/795 424/94.1 |
| 2016/0101390 | A1  | 4/2016 | Chen et al. |

FOREIGN PATENT DOCUMENTS

| CN | 105617460 A | 6/2016 |
| CN | 106962401 A | 7/2017 |
| CN | 106977757 A | 7/2017 |
| CN | 107096068 A | 8/2017 |
| CN | 109342516 A | 2/2019 |
| CN | 109732725 A | 5/2019 |
| CN | 109876673 A | 6/2019 |

OTHER PUBLICATIONS

Sandri et al. "Wound dressings based on silver sulfadiazine solid lipid nanoparticles for tissue repairing" European Journal of Pharmaceutics and Biopharmaceutics. Vo.. 84, Issue 1, May 2013 pp. 84-90 (Year: 2013).*
Liu et al. "Nano-silver-incorporated biomimetic polydopamine coating on a thermoplastic polyurethane porous nanocomposite as an efficient antibacterial wound dressing". Journal of Nanbiotechnology; vol. 16, No. 1, Nov. 2018 (Year: 2018).*
Xu et al. "Polydopamine coatings embedded with silver nanoparticles on nanostructured titania for long-lasing antibacterial effect" Surface and Coatings Technology vol. 320, Jun. 25, 2017, pp. 608-613 (Year: 2017).*
White et al. "Silver sulphadiazine: A review of the evidence." UK: WOunds,; 2005 pp. 55-61 (Year: 2005).*
Peng et al. Microwave-assisted deposition of silver nanoparticles on bamboo pulp fabric through dopamine functionalization. Applied Surface Science. 386. pp 151-159. 2016 (Year: 2016).*
Search Report dated Sep. 16, 2019 and English translation from corresponding application No. CN 201910766453.8.
Liu, Menglong, et al.; Nano-silver-incorporated biomimetic polydopamine coating on a thermoplastic polyurethane porous nanocomposite as an efficient antibacterial wound dressing; Journal of Nanobiotechnology; vol. 16, No. 1, Nov. 18, 2018; 19 pgs.
Gao, Changcheng, et al.; Antibacterial activity and osseointegration of silver-coated poly(ether ether ketone) prepared using the polydopamine-assisted deposition technique; Journal of Materials Chemistry B; vol. 5, No. 47, Jan. 1, 2017; 5 pgs.
Search Opinion issued in European Application No. 20184836.3; mailed Dec. 14, 2020; 3 pgs.

* cited by examiner

| Atomic concentration [%] | | | | |
|---|---|---|---|---|
| Spectrum | C | N | O | Ti |
| sde-5 2714 | 3.68 | 0.00 | 30.74 | 65.58 |
| sde-5 2715 | 2.45 | 0.00 | 32.04 | 65.51 |
| sde-5 2716 | 6.00 | 0.00 | 26.45 | 67.55 |
| Mean | 4.04 | 0.00 | 29.74 | 66.21 |
| Sigma | 1.80 | 0.00 | 2.92 | 1.16 |
| SigmaMean | 1.04 | 0.00 | 1.69 | 0.67 |

POLYDOPAMINE FILM AND PREPARATION METHOD AND APPLICATION THEREOF

TECHNICAL FIELD

The present invention relates to a polydopamine film and a preparation method therefor and an application thereof, and in particular, to a polydopamine film loaded with silver sulfadiazine, a method for preparing the above polydopamine film by in-situ synthesizing silver sulfadiazine on a conventional polydopamine film under microwave irradiation, and an application of the polydopamine film in a medical implant material.

BACKGROUND

Currently, the infection possibly caused when a biomedical implant material is implanted in surgery is still a clinically knotty problem. Due to their excellent mechanical properties and good biocompatibility, biomedical implant materials such as inorganic materials, organic materials and metals and alloy materials thereof (e.g., ceramic, polymer materials, stainless steel, pure titanium and alloys thereof, pure magnesium and alloys thereof, etc.) have been widely used for repairing hard tissues and soft tissues. However, these implant materials themselves do not have antimicrobial and bacteriostatic capabilities, and are liable to cause adhesion of bacteria to their surfaces, thereby leading to the initiation of relevant infections and linkage complications. Postoperative infections often occur even under the conditions, such as, thoroughly sterilized operating room and strictly aseptic surgery. The reason why the biomedical implant materials cause associated infections at a high probability upon implantation, is mainly that it is impossible to ensure absolutely no introduction of bacteria at the time of implanting the biomedical implant materials into bodies. This is especially true for anastomat that is widely used in digestive tract surgery, as it needs to move a longer distance in the digestive tract before reaching the anastomosis site, while the flora inherent in the digestive tract may contaminate the anastomosis nail of the anastomat, thereby causing infection of the anastomosis site and causing inability to heal normally. It can be seen therefrom that loading an appropriate bacteriostatic drug on the surface of the anastomosis nail is an optimal choice for inhibiting the propagation of pathogenic bacteria at the wound site of the digestive tract and promoting wound healing.

In the field of medical apparatus and instruments, a method for loading a drug on the surface of a biomedical implant material is still dominated by a physical coating method, but the interaction force between a physically coated drug layer and a metal substrate, a polymer material or an inorganic material substrate is too weak, and the physically coated drug layer is very easy to peel off. Moreover, chemical loading methods such as a layer-by-layer self-assembly technology are often subject to the physical and chemical properties of the self-assembled film, for example, cold chain storage and cold chain transport are required, and at the same time, the chemical loading methods are less suitable for loading a drug with complex chemical ingredients.

Undergoing a series of reactions, such as self-polymerization under certain conditions, the dopamine can rapidly produce a secure polydopamine film on the surface of almost all substances. The film has an ultra-strong adhesion and good biocompatibility, and since the surface thereof contains a large amount of active functional groups such as catechol and amino groups, this is beneficial for the secondary reaction, that is, a drug can be firmly bonded to the surface of the polydopamine film of an implant material through the action of covalent bonds (Michael addition reaction or Schiff base reaction) or non-covalent bonds (Van der Waals forces, hydrogen bonds, etc.).

The silver sulfadiazine has a broad antibacterial spectrum, and has a good antibacterial activity against most of Gram positive bacteria and negative bacteria. In addition to being used as an external medicament for treating secondary infective wounds of burns or scalds, the silver sulfadiazine can also be used to coat traditional central venous catheters with antibacterial coatings to reduce the incidence of infections, and is widely used. However, conventional methods for synthesizing silver sulfadiazine do not allow the silver sulfadiazine to be coated directly on the polydopamine film. Because the silver sulfadiazine is poorly soluble and is insoluble in water, ethanol, trichloromethane or diethyl ether, the conventional methods for synthesizing silver sulfadiazine are mainly dissolving the insoluble sulfadiazine with sodium hydroxide or aqueous ammonia, and then reacting it with silver nitrate when heated in the presence of a catalyst trifluoromethanesulfonic acid or trifluoromethanesulfonic salt to produce a silver sulfadiazine precipitate. However, the ammonia solution of silver sulfadiazine is corrosive to the polydopamine film, and in particular, aqueous ammonia may cause depolymerization of the polydopamine film and a film solubilization phenomenon. Further, the catalyst trifluoromethanesulfonic acid or trifluoromethanesulfonic salt will attach or bond in a certain amount to the polydopamine film and competes with the silver sulfadiazine for attachment sites, and the trifluoromethanesulfonic acid or trifluoromethanesulfonic salt also has certain toxicity, which is not applicable to the field of medical apparatus and instruments. The above reasons make it difficult to load the silver sulfadiazine on the surface of the biomedical implant material.

The information disclosed in this portion of Background is merely intended to increase the understanding of the general background of the present invention, but should not be considered as acknowledgement or implications in any form that the information constitutes prior art already known to those skilled in the art.

SUMMARY

In order to overcome the drawbacks of the prior art, one of the objects of the present invention is to provide a novel polydopamine film and a preparation method thereof. The polydopamine film is loaded with silver sulfadiazine, and the preparation method achieves in-situ synthesis of silver sulfadiazine on a conventional polydopamine film by microwave irradiation.

It is also an object of the present invention to provide use of the polydopamine films described above in medical implant materials.

It is also an object of the present invention to provide a medical implant material using the above polydopamine film as a coating and a preparation method thereof.

In order to achieve the above objects, the present invention provides the following technical solutions:

A polydopamine film loaded with silver sulfadiazine.

In an implementable embodiment, the polydopamine film described above is free of a catalyst trifluoromethanesulfonic acid or a trifluoromethanesulfonic salt residue.

A method for preparing a polydopamine film, comprising the step of in-situ synthesizing silver sulfadiazine on a conventional polydopamine film, and the step of in-situ synthesizing silver sulfadiazine on a conventional polydopamine film further comprises the steps of:
1. placing a conventional polydopamine film in a sodium hydroxide solution containing sulfadiazine, controlling the pH between 7.1 and 13.0, and reacting the mixture under the conditions of microwave irradiation to obtain an intermediate loaded with the sodium sulfadiazine on the surface, taking out the intermediate, and washing and drying the same; and
2. immersing the material treated in step 1 in a silver nitrate solution, and reacting the mixture under the conditions of microwave irradiation, so that sodium ions in a sodium sulfadiazine molecule are replaced by silver ions in the silver nitrate to obtain a target product loaded with the silver sulfadiazine on the surface, taking out the target product, and washing and drying the same.

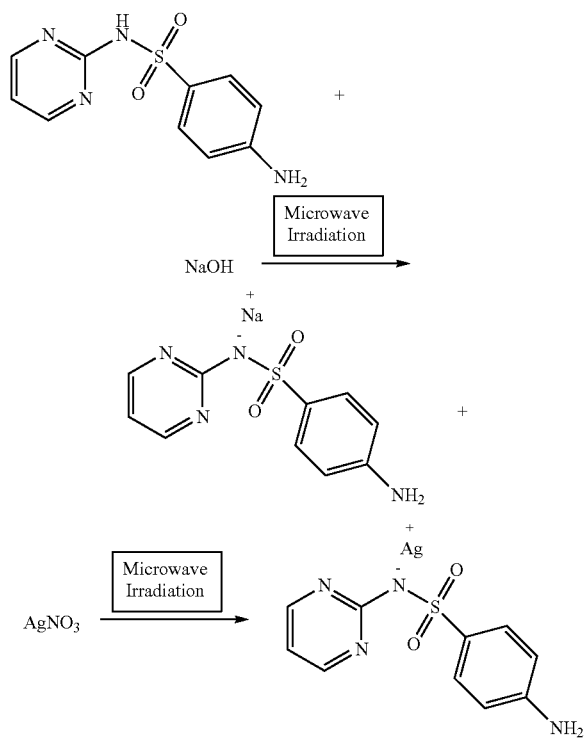

Conventional polydopamine films used in the present invention refer to polydopamine films not loaded with silver sulfadiazine.

In an implementable embodiment, the microwave irradiation in steps 1 and 2 is to cause a reaction by putting a reaction flask charged with a mixture into a cavity of a temperature-controllable focused microwave synthesizer.

The above preparation method of the polydopamine film in an implementable embodiment, the conditions of reacting under the conditions of microwave irradiation are: thermostatic reaction at 25 to 95° C. for 0.3 to 30 minutes, and the microwave power of 100 to 1500 W.

The above preparation method of the polydopamine film in an implementable embodiment, the molar ratio of sulfadiazine to sodium hydroxide is 1:1 to 5.

The above preparation method of the polydopamine film in an implementable embodiment, the molar ratio of sulfadiazine to silver nitrate is 1:1 to 5.

Use of the polydopamine films described above in medical implant materials.

The above use in an implementable embodiment, the medical implant material comprises an anastomat, and further comprises an anastomosis nail of the anastomat.

The above use in an implementable embodiment, the medical implant material comprises at least one of an inorganic material, an organic material and a metal material; optionally, the texture of the medical implant material comprises at least one of ceramic, a polymer material, stainless steel, pure titanium and alloys thereof, pure magnesium and alloys thereof.

A medical implant material, comprising the above polydopamine film as a coating.

The above medical implant material in an implementable embodiment, the polydopamine film has one, two or more layers.

The above medical implant material in an implementable embodiment, the medical implant material comprises an anastomat, and further comprises an anastomosis nail of the anastomat.

In an implementable embodiment, the medical implant material comprises at least one of an inorganic material, an organic material and a metal material; optionally, the material of the medical implant material comprises at least one of ceramic, a polymer material, stainless steel, pure titanium and alloys thereof, pure magnesium and alloys thereof.

A method for preparing a medical implant material, comprising the steps of:
1. preparing a conventional polydopamine film as a coating on the surface of a medical implant material:
2. in-situ synthesizing silver sulfadiazine on a conventional polydopamine film according to the above-mentioned preparation method of the polydopamine film.

The above preparation method for the medical implant material in an implementable embodiment, the step of preparing a conventional polydopamine film as a coating on the surface of a medical implant material comprises: sterilizing the cleaned medical implant material; then immersing the sterilized material in a dopamine monomer buffer solution at pH 7.1 to 13.0, reacting the mixture under the conditions of microwave irradiation so as to form a polydopamine film on the surface of the medical implant material, taking out the medical implant material, and washing and drying the same.

The above preparation method for the medical implant material in an implementable embodiment, calcium peroxide is further added as an oxidizing agent in a dopamine monomer buffer solution, in which the medical implant material is immersed; optionally, the concentration of the calcium peroxide in the dopamine monomer buffer solution is 10 to 100 mg/L.

The above preparation method for the medical implant material in an implementable embodiment, the microwave irradiation is performing a reaction by putting a reaction flask charged with a mixture into a cavity of a temperature-controllable focused microwave synthesizer.

The above preparation method for the medical implant material in an implementable embodiment, the conditions of sterilizing the cleaned medical implant material, then soaking the sterilized material in a dopamine monomer buffer solution at pH 7.1 to 13.0, and reacting the mixture under the conditions of microwave irradiation are: thermostatic reaction at 25 to 95° C. for 0.3 to 30 minutes, and the microwave power of 100 to 1500 W.

The above preparation method for the medical implant material in an implementable embodiment, the concentration of the dopamine monomer in the dopamine monomer buffer solution is 0.5 to 10 g/L, optionally 1 to 7 g/L.

The above preparation method for the medical implant material in an implementable embodiment, the step of preparing a conventional polydopamine film as a coating on the surface of the medical implant material is performed once, twice or more times in order to have at least one layer of polydopamine film.

The above preparation method for the medical implant material in an implementable embodiment, the medical implant material comprises an anastomat, and further comprises an anastomosis nail of the anastomat.

The above preparation method for the medical implant material in an implementable embodiment, the texture of the medical implant material comprises at least one of an inorganic material, an organic material and a metal material; optionally, the texture of the medical implant material comprises at least one of ceramic, a polymer material, stainless steel, pure titanium and alloys thereof, pure magnesium and alloys thereof.

The above preparation method for the medical implant material in an implementable embodiment, the sterilizing method is: irradiating under ultraviolet light for 0.1 to 24 hours.

The above preparation method for the medical implant material in an implementable embodiment, the dopamine monomer buffer solution is a dopamine monomer Tris-HCL solution.

Compared with the prior art, the present invention has the following beneficial effects:
1. The present invention places a conventional polydopamine film in a sodium hydroxide solution containing sulfadiazine. Under microwave irradiation in combination with covalent binding via a Michael addition reaction or a Schiff base reaction and non-covalent binding including van der Waals' force, hydrogen bond and the like, sodium sulfadiazine is uniformly and firmly loaded on the surface of the conventional polydopamine film, which is immersed in the reaction liquid. By washing with water repeatedly, it is possible to remove the unstable sodium sulfadiazine and the free sodium sulfadiazine, and then to obtain a polydopamine film loaded with sulfadiazine sodium. Thereafter, the polydopamine film loaded with sodium sulfadiazine is placed in a silver nitrate solution, and subjected to microwave irradiation. The sodium ions in the sodium sulfadiazine are replaced by silver ions to generate silver sulfadiazine, while the sodium ions and the nitrate form soluble sodium nitrate, which can be removed, and finally the silver sulfadiazine is in-situ synthesized on the surface of a conventional polydopamine film.

The microwave irradiation itself has the following advantages: (1) it accelerates the synthesis reaction; especially when silver sulfadiazine is synthesized in situ, microwave irradiation can increase the probability of contacting, reacting and binding silver ions of silver nitrate with the secure sulfadiazine loaded on the polydopamine film by thousands of times, which greatly promotes the synthesis of silver sulfadiazine, shortens the time of in-situ synthesizing silver sulfadiazine on the surface of the polydopamine film, and simplifies the step of in-situ synthesizing silver sulfadiazine on the surface of the polydopamine film; (2) because of the use of microwave irradiation, no physical stirring and external warming are required in the reaction, thereby achieving stirring at a molecular level and high reaction yield; (3) it is environmentally friendly, contamination-free, clean, and convenient, which belongs to green chemistry; and (4) its process is simple and easy to implement under mild conditions.

In the method, the sulfadiazine is not dissolved with traditional aqueous ammonia, which has the following advantages: firstly, preventing the polydopamine film from being corroded by the aqueous ammonia; secondly, protecting mucosa such as eyes and nasal cavities of workers from stimulation and corrosion of the aqueous ammonia: and thirdly, avoiding the environmental problem caused by pungent odor and fumes emitted from high-concentration aqueous ammonia.

In the method, without using the catalyst trifluoromethanesulfonic acid or trifluoromethanesulfonic salt, not only is the loading of silver sulfadiazine increased, but also the safety performance can be further improved.

2. Modifying the surface of the medical implant material with a polydopamine film makes use of the characteristics including film self-polymerization, attachment, film formation, film surface functionalization, and the like of the polydopamine film. A conventional preparation method for the polydopamine film is as follows: exposing to oxygen in the air or oxygen charged at high pressure or some oxidizing agent added in a weakly alkaline solution, the active catechol group inside the dopamine monomer molecule is oxidized by dissolved oxygen, and initiates self-polymerization and cross-linking reactions to generate oligomers having different molecular weights. The oligomers are further oxidized, self-polymerized and cross-linked, thereby producing polymers having high molecular weights, in the meantime, under the synergism of a plurality of covalent and non-covalent bonds possessed by the polymers, closely adhered composite films are formed on the surface of a medical implant material. However, the disadvantage of this method for preparing a polydopamine film is that the reaction period is very long, specifically, complete formation of the polydopamine film generally takes at least 24 hours, so the medical implant material needs to be immersed for 24 hours or longer in a weakly alkaline solution of the dopamine monomer in order to obtain the target product. Such a long period indicates that the probability for the reaction liquid being contaminated by bacteria increases, and pyrogen (endotoxin) is generated and also adhere to the polydopamine film, which causes disqualification of the pyrogen test of the product, while the nation imposes very strict requirements for the pyrogen tests of the medical implant materials. Therefore, shortening the production time of the polydopamine film has a realistic meaning. The technical solution concerning calcium peroxide and/or microwave irradiation employed in the present invention can ensure that a pyrogen-free and intact polydopamine film is prepared in a short time.

(1) A microwave has high frequency, fluctuation, thermal and non-thermal properties, and the effect of inducing oxygenation synthesis, and can accelerate the organic chemical reaction. Microwave irradiation, which acts on the dopamine monomer and oxygen, causes changes in energy level in molecule. The dopamine monomer and the oxygen molecule obtain energy and transit into a metastable state. The molecule vibrates and rotates, so that the effective collision frequency between the catechol groups of dopamine and between the catechol group of dopamine and the oxygen molecule greatly increases, thereby accelerating the reaction, and shortening the time of forming a polydopamine film. Meanwhile, due to the "bulk heating effect" of the microwave, all parts of the reactants are heated more quickly and more uniformly, and the polymerization rate is greatly accelerated, so that the dopamine monomer is completely polymerized in a short time and forms an intact polydopamine film, in the absence of physical stirring and external warming, thereby achieving stirring at a molecular level, also reducing the by-products in the reaction and increasing the yield. As microwave irradiation allows for thorough oxidization, polymerization and crosslinking reactions, the resulting polydopamine film has good adhesion, stability and functionality, and can withstand ultrasonic cleaning. Further, microwave irradiation is clean, convenient, non-pyrogenic, and environmentally friendly, so it belongs to green chemistry. Still further, its process is simple and easy to implement under mild conditions.

(2) Compared with other oxidizing agents, calcium peroxide has three advantages: one is that it, in contact with water, emits oxygen, and can instantaneously provide a large amount of oxygen required for the reaction, and can also accelerate the oxidation, polymerization and crosslinking reactions. The second is that it has a certain bacteriostatic effect. The third is that the final product of the reaction is calcium oxide, which is non-toxic, and meanwhile, the free calcium ions can be chelated with a catechol group of dopamine to fill the excess chelation sites, without binding metals, left on the film surface after binding to sodium sulfadiazine.

3. The step of preparing a polydopamine film as a coating on the surface of the medical implant material is performed two or more times, and the polydopamine film can be thickened to a desired thickness.

DETAILED DESCRIPTION

Figure 1A:
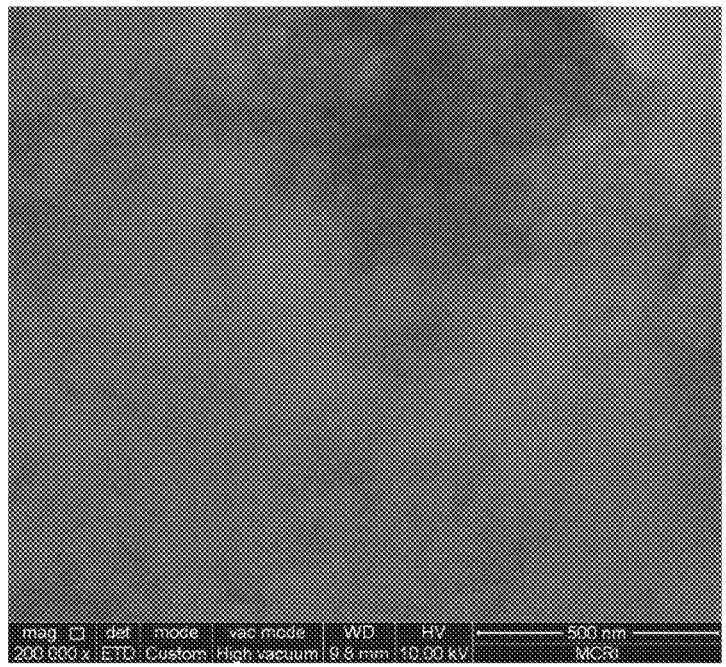
FIG. 1A is a field emission scanning electron microscope diagram of a polydopamine film in-situ synthesized with silver sulfadiazine in Example 1.

Hereinafter, specific embodiments of the present invention will be described in detail with reference to the accompanying drawings, but it should be understood that the scope of protection for the present invention is not subject to the specific embodiments.

Unless otherwise expressly indicated, throughout the specification and claims, the term "comprising" or variations thereof, such as "containing" or "including", will be construed as comprising the stated elements or components, but not excluding other elements or other components.

Example 1

1. Preparation of Polydopamine Coating:
1.1 The washed and cleaned pure titanium medical implant material was irradiated under ultraviolet rays for 1 hour, and then immersed in a Tris-HCL solution containing 2 g/L of dopamine monomer at pH 8.5, to which calcium peroxide at a final concentration of 10 mg/L was added. The reaction flask charged with the mixed liquid was immediately put into the cavity of a temperature-controllable focused microwave synthesizer, and thereafter subjected to a thermostatic reaction at 25° C. for 3 minutes, wherein the microwave power was 300 W. Then a dense polydopamine film could be formed on the surface of the implant. The dense polydopamine film was taken out, ultrasonically washed repeatedly and rinsed in deionized water, and dried under nitrogen.

1.2 Step 1.1 was not Repeated. The Polydopamine Film was a Single Layer.

2. In-Situ Synthesis of Silver Sulfadiazine on Conventional Polydopamine Films 2.1 The material treated in step 1.2 was placed in a solution of sulfadiazine (20 mmol/L) in sodium hydroxide (20 mmol/L) at pH 8.3, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 35° C. for 3 minutes, wherein the microwave power was 300 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (20 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 35° C. for 3 minutes, wherein the microwave power was 300 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 2

1. Preparation of Polydopamine Coating:
1.1 The washed and cleaned titanium alloy (TI-6AL-4V) medical implant material was irradiated under ultraviolet rays for 6 hours, and then immersed in a Tri-HCL solution containing 1 g/L of dopamine monomer at pH 7.1, to which calcium peroxide at a final concentration of 20 mg/L was added. The reaction flask charged with the mixed liquid was immediately put into the cavity of a temperature-controllable focused microwave synthesizer, and thereafter subjected to a thermostatic reaction at 65° C. for 5 minutes, wherein the microwave power was 100 W. Then a dense polydopamine film could be formed on the surface of the implant. The dense polydopamine film was taken out, ultrasonically washed repeatedly and rinsed in deionized water, and dried under nitrogen.

1.2 Step 1.1 was repeated 4 times. The final polydopamine film had 5 layers.

2. In-situ Synthesis of Silver Sulfadiazine on Conventional Polydopamine Films 2.1 The material treated in step 1.2 was placed in a solution of sulfadiazine (30 mmol/L) in sodium hydroxide (45 mmol/L) at pH 8.7, and the molar ratio of sulfadiazine and sodium hydroxide was 1:1.5. The reaction flask charged with the mixed liquid was immediately put into the cavity of a temperature-controllable focused microwave synthesizer, and thereafter subjected to a thermostatic reaction at 55° C. for 10 minutes, wherein the microwave power was 100 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (60 mmol/L), such that the molar ratio of silver nitrate to the sulfadiazine in step 2.1 was 2:1. The reaction flask charged with the mixed liquid was immediately put into the cavity of a temperature-controllable focused microwave synthesizer, and thereafter subjected to a thermostatic reaction at 55° C. for 10 minutes, wherein the microwave power was 100 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 3

1. Preparation of Polydopamine Coating:
1.1 The washed and cleaned titanium alloy (Ti-25nb-10ta-1zr-0.2fe) medical implant material was irradiated under ultraviolet rays for 12 hours, and then immersed in a Tris-HCL solution containing 3 g/L of dopamine monomer Tri-HCL at pH 8.0, to which calcium peroxide at a final concentration of 40 mg/L was added. The reaction flask charged with the mixed liquid was immediately put into the cavity of a temperature-controllable focused microwave synthesizer, and thereafter subjected to a thermostatic reaction at 50° C. for 11 minutes, wherein the microwave power was 100 W. Then a dense polydopamine film could be formed on the surface of the implant. The dense polydopamine film was taken out, ultrasonically washed repeatedly and rinsed in deionized water, and dried under nitrogen.

1.2 Step 1.1 was repeated 9 times. The final polydopamine film had 10 layers.

2. In-situ Synthesis of Silver Sulfadiazine on Conventional Polydopamine Films 2.1 The material treated in step 1.2 was placed in a solution of sulfadiazine (10 mmol/L) in sodium hydroxide (30 mmol/L) at pH 9.6, and the molar ratio of sulfadiazine and sodium hydroxide was 1:3. The reaction flask charged with the mixed liquid was immediately put into the cavity of a temperature-controllable focused microwave synthesizer, and thereafter subjected to a thermostatic reaction at 60° C. for 12 minutes, wherein the microwave power was 400 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (50 mmol/L), such that the molar ratio of silver nitrate to the sulfadiazine in step 2.1 was 5:1. The reaction flask charged with the mixed liquid was immediately put into the cavity of a temperature-controllable focused microwave synthesizer, and thereafter subjected to a thermostatic reaction at 75° C. for 12 minutes, wherein the microwave power was 400 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 4

1. Preparation of Polydopamine Coating:
1.1 The washed and cleaned medical implant ceramic was irradiated with ultraviolet rays for 24 hours, and then immersed in a Tris-HCL solution containing 7 g/L of dopamine monomer Tris-HCL at pH 9.5, to which calcium peroxide at a final concentration of 60 mg/L was added. The reaction flask charged with the mixed liquid was immediately put into the cavity of a temperature-controllable focused microwave synthesizer, and thereafter subjected to a thermostatic reaction at 65° C. for 20 minutes, wherein the microwave power was 1200 W. Then a dense polydopamine film could be formed on the surface of the implant. The dense polydopamine film was taken out, ultrasonically washed repeatedly and rinsed in deionized water, and dried under nitrogen.

1.2 Step 1.1 was repeated 19 times. The final polydopamine film had 20 layers.

2. In-situ Synthesis of Silver Sulfadiazine on Conventional Polydopamine Films 2.1 The material treated in step 1.2 was placed in a solution of sulfadiazine (70 mmol/L) in sodium hydroxide (105 mmol/L) at pH 11.0, and the molar ratio of sulfadiazine and sodium hydroxide was 1:1.5. The reaction flask charged with the mixed liquid was immediately put into the cavity of a temperature-controllable focused microwave synthesizer, and thereafter subjected to a thermostatic reaction at 55° C. for 16.7 minutes, wherein the microwave power was 1,000 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (70 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 95° C. for 30 minutes, wherein the microwave power was 1,000 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 5

1. Preparation of Polydopamine Coating:
1.1 The washed and cleaned bioengineering medical implant ceramic was irradiated under ultraviolet rays for 18 hours, and then immersed in a Tris-HCL solution containing 2.5 g/L dopamine monomer at pH 10.1, to which calcium peroxide at a final concentration of 70 mg/L was added. The reaction flask charged with the mixed liquid was immediately put into the cavity of a temperature-controllable focused microwave synthesizer, and thereafter subjected to a thermostatic reaction at 25° C. for 4 minutes, wherein the microwave power was 300 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 8 Times. The Final Polydopamine Film had 9 Layers.

2. In-Situ Synthesis of Silver Sulfadiazine on Conventional Polydopamine Films 2.1 The material treated in step 1.2 was placed in a solution of sulfadiazine (25 mmol/L) in sodium hydroxide (50 mmol/L) at pH 8.3, and the molar ratio of sulfadiazine and sodium hydroxide was 1:2. The reaction flask charged with the mixed liquid was immediately put into the cavity of a temperature-controllable focused microwave synthesizer, and thereafter subjected to a thermostatic reaction at 65° C. for 8 minutes, wherein the microwave power was 1,500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (25 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 65° C. for 12 minutes, wherein the microwave power was 1,500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 6

1. Preparation of Polydopamine Coating:
1.1 The washed and cleaned pure titanium medical implant material was irradiated under ultraviolet rays for 12 hours, and then immersed in a Tris-HCL solution containing 2 g/L of dopamine monomer at pH 8.5, to which calcium peroxide at a final concentration of 90 mg/L was added. The reaction flask charged with the mixed liquid was immediately put into the cavity of a temperature-controllable focused microwave synthesizer, and thereafter subjected to a thermostatic reaction at 25° C. for 9 minutes, wherein the microwave power is 300 W. The dense polydopamine film was taken out, ultrasonically washed repeatedly and rinsed in deionized water, and dried under nitrogen.

1.2 Step 1.1 was not Repeated. The Polydopamine Film was a Single Layer.

2. In-Situ Synthesis of Silver Sulfadiazine on Conventional Polydopamine Films
2.1 The material treated in step 1.2 was placed in a solution of sulfadiazine (20 mmol/L) in sodium hydroxide (40 mmol/L) at pH 8.9, and the molar ratio of sulfadiazine and sodium hydroxide was 1:2. The reaction flask charged with the mixed liquid was immediately put into the cavity of a temperature-controllable focused microwave synthesizer, and thereafter subjected to a thermostatic reaction at 45° C. for 10 minutes, wherein the microwave power was 300 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (20 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 80° C. for 4 minutes, wherein the microwave power was 300 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 7

1. Preparation of Polydopamine Coating:
1.1 The washed and cleaned pure medical implant material ceramic was irradiated under ultraviolet rays for 18 hours, and then immersed in a Tris-HCL solution containing 3.5 g/L of dopamine monomer at pH 8.5, to which calcium peroxide at a final concentration of 100 mg/1, was added. The reaction flask charged with the mixed liquid was immediately put into the cavity of a temperature-controllable focused microwave synthesizer, and thereafter subjected to a thermostatic reaction at 65° C. for 25 minutes, wherein the microwave power is 1300 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 4 Times. The Final Polydopamine Film had 5 Layers.

2. In-Situ Synthesis of Silver Sulfadiazine on Conventional Polydopamine Films
2.1 The material treated in step 1.2 was placed in a solution of sulfadiazine (60 mmol/L) in sodium hydroxide (180 mmol/L) at pH 8.3, and the molar ratio of sulfadiazine and sodium hydroxide was 1:3. The reaction flask charged with the mixed liquid was immediately put into the cavity of a temperature-controllable focused microwave synthesizer, and thereafter subjected to a thermostatic reaction at 60° C. for 30 minutes, wherein the microwave power was 500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (60 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 70° C. for 30 minutes, wherein the microwave power was 500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 8

1. Preparation of Polydopamine Coating:
1.1 The washed and cleaned bioengineering medical implant ceramic was irradiated with ultraviolet rays for 24 hours, and then immersed in a Tris-HCL solution containing 2.5 g/L dopamine monomer at pH 10.1, to which calcium peroxide at a final concentration of 70 mg/L was added. The reaction flask charged with the mixed liquid was immediately put into the cavity of a temperature-controllable focused microwave synthesizer, and thereafter subjected to a thermostatic reaction at 30° C. for 16 minutes, wherein the microwave power is 300 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 12 Times. The Final Polydopamine Film had 13 Layers.

2. In-Situ Synthesis of Silver Sulfadiazine on Conventional Polydopamine Films 2.1 The material treated in step 1.2 was placed in a solution of sulfadiazine (25 mmol/L) in sodium hydroxide (75 mmol/L) at pH 10.5, and the molar ratio of sulfadiazine and sodium hydroxide was 1:3. The reaction flask charged with the mixed liquid was immediately put into the cavity of a temperature-controllable focused microwave synthesizer, and thereafter subjected to a thermostatic reaction at 65° C. for 25 minutes, wherein the microwave power was 1,100 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (25 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 65° C. for 30 minutes, wherein the microwave power was 1,100 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 9

1. Preparation of Polydopamine Coating:

1.1 The washed and cleaned Si medical implant material was irradiated under ultraviolet rays for 1 hour, and then immersed in a Tris-HCL solution containing 2.5 g/L dopamine monomer at pH 8.5, to which calcium peroxide at a final concentration of 60 mg/L was added. The reaction flask charged with the mixed liquid was immediately put into the cavity of a temperature-controllable focused microwave synthesizer, and thereafter subjected to a thermostatic reaction at 40° C. for 10 minutes, wherein the microwave power is 600 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 7 Times. The Final Polydopamine Film had 8 Layers.

2. In-Situ Synthesis of Silver Sulfadiazine on Conventional Polydopamine Films 2.1 The material treated in step 1.2 was placed in a solution of sulfadiazine (25 mmol/L) in sodium hydroxide (50 mmol/L) at pH 8.3, and the molar ratio of sulfadiazine and sodium hydroxide was 1:2. The reaction flask charged with the mixed liquid was immediately put into the cavity of a temperature-controllable focused microwave synthesizer, and thereafter subjected to a thermostatic reaction at 45° C. for 20 minutes, wherein the microwave power was 500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (25 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 65° C. for 20 minutes, wherein the microwave power was 500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 10

1. Preparation of Polydopamine Coating:

1.1 The washed and cleaned stainless steel medical implant material was irradiated with ultraviolet rays for 8 hours, and then immersed in a Tris-HCL solution containing 5.5 g/L dopamine monomer at pH 10.5, to which calcium peroxide at a final concentration of 90 mg/L was added. The reaction flask charged with the mixed liquid was immediately put into the cavity of a temperature-controllable focused microwave synthesizer, and thereafter subjected to a thermostatic reaction at 25° C. for 4 minutes, wherein the microwave power is 600 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated Once. The Final Polydopamine Film had 2 Layers.

2. In-Situ Synthesis of Silver Sulfadiazine on Conventional Polydopamine Films 2.1 The material treated in step 1.2 was placed in a solution of sulfadiazine (5 mmol/L) in sodium hydroxide (25 mmol/L) at pH 11.0, and the molar ratio of sulfadiazine and sodium hydroxide was 1:5. The reaction flask charged with the mixed liquid was immediately put into the cavity of a temperature-controllable focused microwave synthesizer, and thereafter subjected to a thermostatic reaction at 65° C. for 5 minutes, wherein the microwave power was 1,500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (5 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 65° C. for 12.5 minutes, wherein the microwave power was 1,500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 11

1. Preparation of Polydopamine Coating:

1.1 The washed and cleaned stainless steel medical implant material was irradiated under ultraviolet rays for 6 hours, and then immersed in a Tris-HCL solution containing 2.5 g/L dopamine monomer at pH 7.1, to which calcium peroxide at a final concentration of 50 mg/L was added. The reaction flask charged with the mixed liquid was immediately put into the cavity of a temperature-controllable focused microwave synthesizer, and thereafter subjected to a thermostatic reaction at 60° C. for 25 minutes, wherein the microwave power was 900 W. Then a dense polydopamine film can be obtained on the surface of the implant. The dense polydopamine film was taken out, ultrasonically washed repeatedly and rinsed in deionized water, and dried under nitrogen.

1.2 Step 1.1 was Repeated 8 Limes. The Final Polydopamine Film had 9 Layers.

2. In-Situ Synthesis of Silver Sulfadiazine on Conventional Polydopamine Films 2.1 The material treated in step 1.2 was placed in a solution of sulfadiazine (20 mmol/L) in sodium hydroxide (50 mmol/L) at pH 8.9, and the molar ratio of sulfadiazine and sodium hydroxide was 1:2.5. The reaction flask charged with the mixed liquid was immediately put into the cavity of a temperature-controllable focused microwave synthesizer, and thereafter subjected to a thermostatic reaction at 50° C. for 12 minutes, wherein the microwave power was 700 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (20 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 50° C. for 30 minutes, wherein the microwave power was 700 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 12

1. Preparation of Polydopamine Coating:

1.1 The washed and cleaned polyurethane medical implant material was irradiated under ultraviolet rays for 0.5 hours, and then immersed in a Tris-HCL solution containing 2.5 g/L dopamine monomer at pH 8.5, to which calcium peroxide at a final concentration of 15 mg/L was added. The reaction flask charged with the mixed liquid was immediately put into the cavity of a temperature-controllable focused microwave synthesizer, and thereafter subjected to a thermostatic reaction at 25° C. for 6 minutes, wherein the microwave power was 300 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated Twice, the Final Polydopamine Film had 3 Layers.

2. In-Situ Synthesis of Silver Sulfadiazine on Conventional Polydopamine Films 2.1 The material treated in step 1.2 was placed in a solution of sulfadiazine (20 mmol/L) in sodium hydroxide (20 mmol/L) at pH 8.1, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 75° C. for 15 minutes, wherein the microwave power was 200 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (20 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 95° C. for 5 minutes, wherein the microwave power was 200 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 13

1. Preparation of Polydopamine Coating:

1.1 The washed and cleaned silicone rubber medical implant material was irradiated under ultraviolet rays for 0.1 hours, and then immersed in a Tris-HCL solution containing 3.0 g/L of dopamine monomer at pH 8.5, to which calcium peroxide at a final concentration of 10 mg/L was added. The reaction flask charged with the mixed liquid was immediately put into the cavity of a temperature-controllable focused microwave synthesizer, and thereafter subjected to a thermostatic reaction at 30° C. for 15 minutes, wherein the microwave power was 300 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 11 Times. The Final Polydopamine Film had 12 Layers.

2. In-Situ Synthesis of Silver Sulfadiazine on Conventional Polydopamine Films 2.1 The material treated in step 1.2 was placed in a solution of sulfadiazine (20 mmol/L) in sodium hydroxide (20 mmol/L) at pH 8.4, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 65° C. for 20 minutes, wherein the microwave power was 600 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (20 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 75° C. for 21.7 minutes, wherein the microwave power was 600 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 14

1. Preparation of Polydopamine Coating:

1.1 The washed and cleaned polyester-based medical implant material was irradiated with ultraviolet rays for 0.3 hours, and then immersed in a Tris-HCL solution containing 4.5 g/L of dopamine monomer at pH 8.5, to which calcium peroxide at a final concentration of 20 mg/L was added. The reaction flask charged with the mixed liquid was immediately put into the cavity of a temperature-controllable focused microwave synthesizer, and thereafter subjected to a thermostatic reaction at 55° C. for 13.3 minutes, wherein the microwave power was 200 W. Then a dense polydopamine film could be formed on the surface of the implant. The dense polydopamine film was taken out, ultrasonically washed repeatedly and rinsed in deionized water, and dried under nitrogen.

1.2 Step 1.1 was Repeated 6 Times. The Final Polydopamine Film had 7 Layers.

2. In-Situ Synthesis of Silver Sulfadiazine on Conventional Polydopamine Films 2.1 The material treated in step 1.2 was placed in a solution of sulfadiazine (25 mmol/L) in sodium hydroxide (25 mmol/L) at pH 8.3, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 35° C. for 30 minutes, wherein the microwave power was 100 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (25 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 55° C. for 20 minutes, wherein the microwave power was 100 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 15

1. Preparation of Polydopamine Coating:

1.1 The washed and cleaned pure titanium medical implant material was irradiated under ultraviolet rays for 12 hours, and then immersed in a Tris-HCL solution containing 2.5 g/L of dopamine monomer at pH 9.5, to which calcium peroxide at a final concentration of 30 mg/L was added. The reaction flask charged with the mixed liquid was immediately put into the cavity of a temperature-controllable focused microwave synthesizer, and thereafter subjected to a thermostatic reaction at 25° C. for 9 minutes, wherein the microwave power was 1500 W. Then a dense polydopamine film can be obtained on the surface of the implant. The dense polydopamine film was taken out, ultrasonically washed repeatedly and rinsed in deionized water, and dried under nitrogen.

1.2 Step 1.1 was Repeated 4 Times. The Final Polydopamine Film had 5 Layers.

2. In-Situ Synthesis of Silver Sulfadiazine on Conventional Polydopamine Films 2.1 The material treated in step 1.2 was placed in a solution of sulfadiazine (40 mmol/L) in sodium hydroxide (40 mmol/L) at pH 8.9, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 25° C. for 25 minutes, wherein the microwave power was 1,500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (40 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 65° C. for 16 minutes, wherein the microwave power was 1,500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 16

1. Preparation of Polydopamine Coating:

1.1 The washed and cleaned pure titanium medical implant material was irradiated under ultraviolet rays for 20 hours, and then immersed in a Tris-HCL solution containing 6.5 g/L of dopamine monomer at pH 9.0, to which calcium peroxide at a final concentration of 30 mg/L was added. The reaction flask charged with the mixed liquid was immediately put into the cavity of a temperature-controllable focused microwave synthesizer, and thereafter subjected to a thermostatic reaction at 65° C. for 3 minutes, wherein the microwave power was 700 W. Then a dense polydopamine film can be obtained on the surface of the implant. The dense polydopamine film was taken out, ultrasonically washed repeatedly and rinsed in deionized water, and dried under nitrogen.

1.2 Step 1.1 was not repeated. The polydopamine film was a single layer.

2. In-situ Synthesis of Silver Sulfadiazine on Conventional Polydopamine Films 2.1 The material treated in step 1.2 was placed in a solution of sulfadiazine (35 mmol/L) in sodium hydroxide (70 mmol/L) at pH 10.8, and the molar ratio of sulfadiazine and sodium hydroxide was 1:1. The reaction flask charged with the mixed liquid was immediately put into the cavity of a temperature-controllable focused microwave synthesizer, and thereafter subjected to a thermostatic reaction at 65° C. for 10 minutes, wherein the microwave power was 500 W. An intermediate loaded with sulfadiazine sodium on the surface thereof was obtained. The intermediate was taken out, ultrasonically washed repeatedly to remove unbound sodium sulfadiazine, rinsed in deionized water, and dried under nitrogen.

2.2 The material treated in step 2.1 was immersed in a silver nitrate solution (35 mmol/L), such that the molar ratio of silver nitrate to the sulfadiazine in step 2.1 was 1:1. The reaction flask charged with the mixed liquid was immediately put into the cavity of a temperature-controllable focused microwave synthesizer, and thereafter subjected to a thermostatic reaction at 95° C. for 5 minutes, wherein the microwave power was 500 W, so that the sodium ions in the sulfadiazine sodium molecule were replaced by silver ions in silver nitrate, to obtain a target product loaded with silver sulfadiazine on the surface. The target product was taken out, ultrasonically washed repeatedly, rinsed in deionized water, and dried under nitrogen.

Example 17

Characterization of Polydopamine Films with Silver Sulfadiazine In-Situ Synthesized Thereon The present invention used a new method to prepare a functionalized polydopamine film on the surface of a medical implant such as pure titanium, and took advantage of a large amount of active functional groups such as catechol, amino groups and hydroxyl groups included in the polydopamine to cause sulfadiazine to be firmly bonded to the surface of the functionalized polydopamine film, followed by in-situ synthesizing silver sulfadiazine, thereby producing a new material. Experiments on characterization were performed using a field emission scanning electron microscope, X-ray photoelectron spectrogram, and high performance liquid chromatography.

Figure 1B:
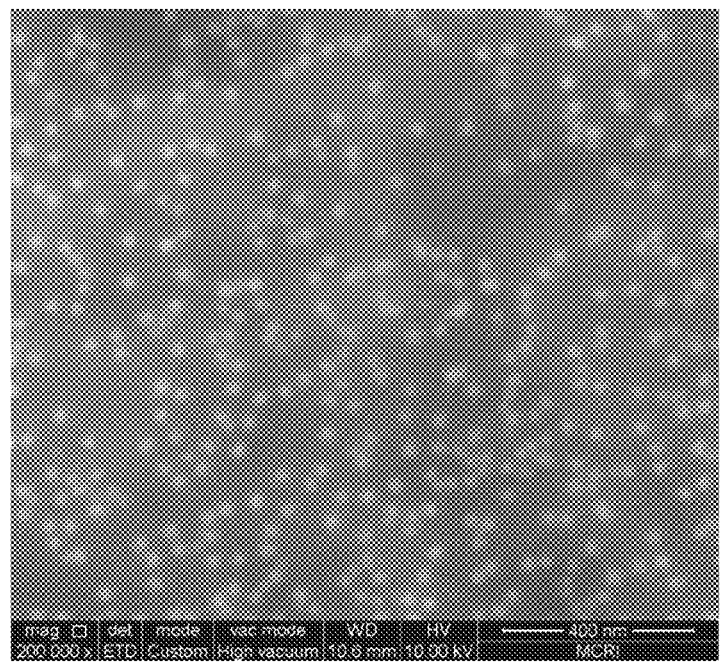
FIG. 1B is an enlarged local view of FIG. 1A.
Figure 2A:
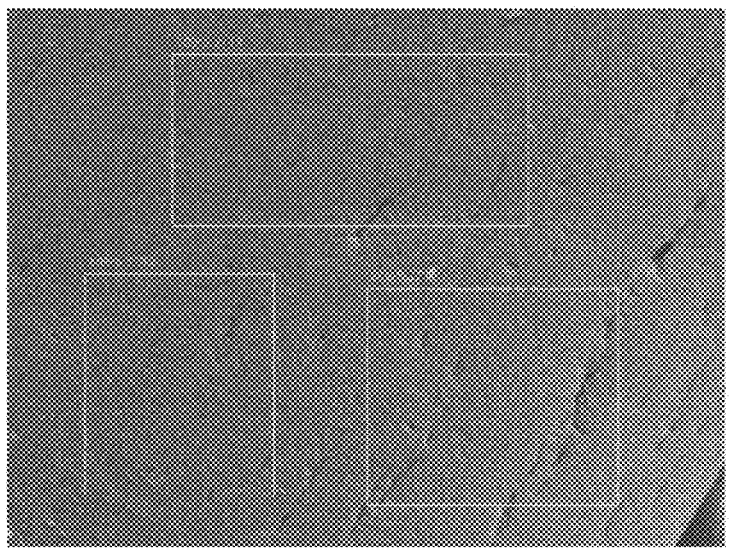
FIG. 2A to FIG. 2C are X-ray photoelectron spectrogram and data diagrams of bare titanium surfaces attached with the polydopamine film, and of polydopamine films in-situ synthesized silver sulfadiazine after the sulfadiazine reacts with the polydopamine film of the bare titanium surface in an alkaline solution in Example 1, in this order. The sde-5 numbers in the data diagrams in FIGS. 2A to 2C indicate numbers of samples taken from the corresponding frame line positions at the left side of the data diagrams, respectively.
Figure 2A:
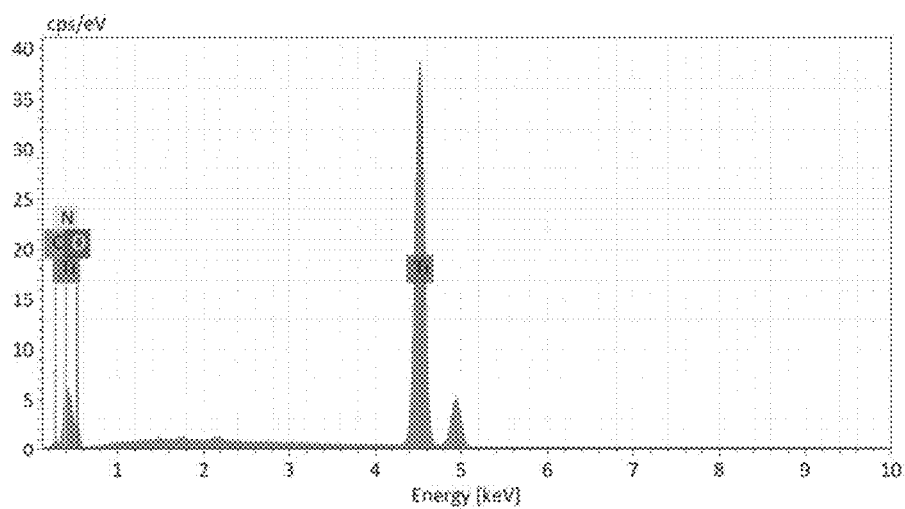
Figure 2B:
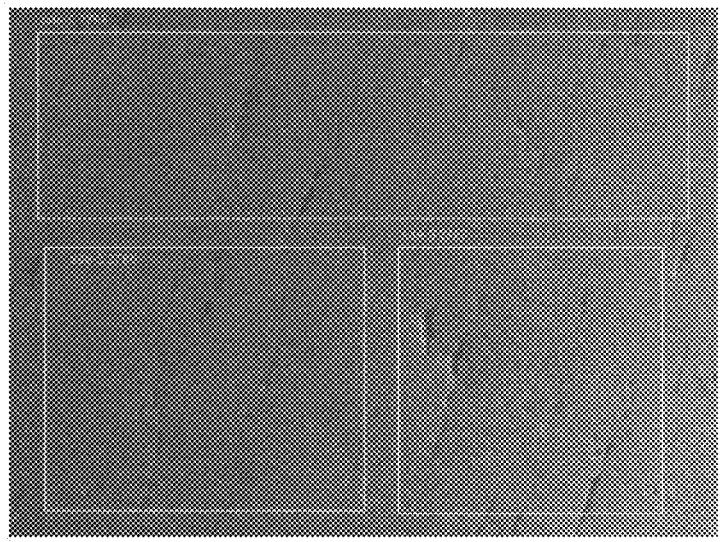
Figure 2B:
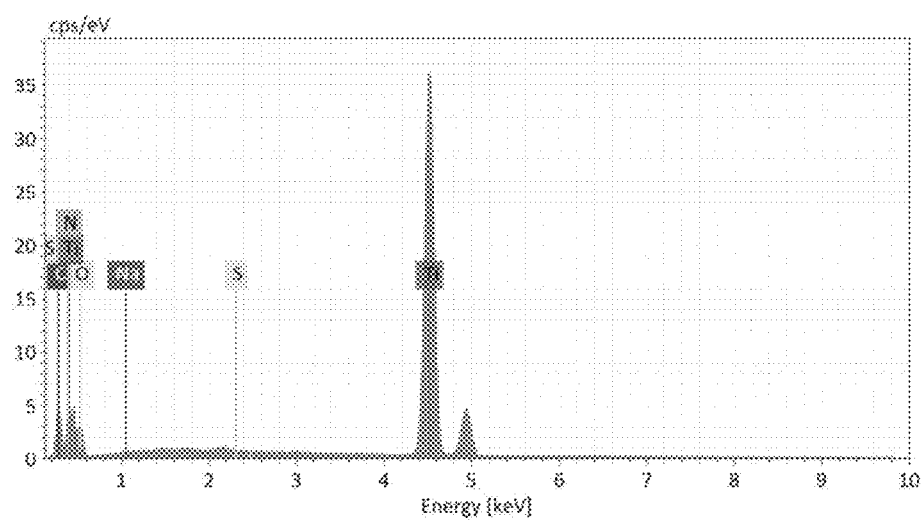
Figure 2C:
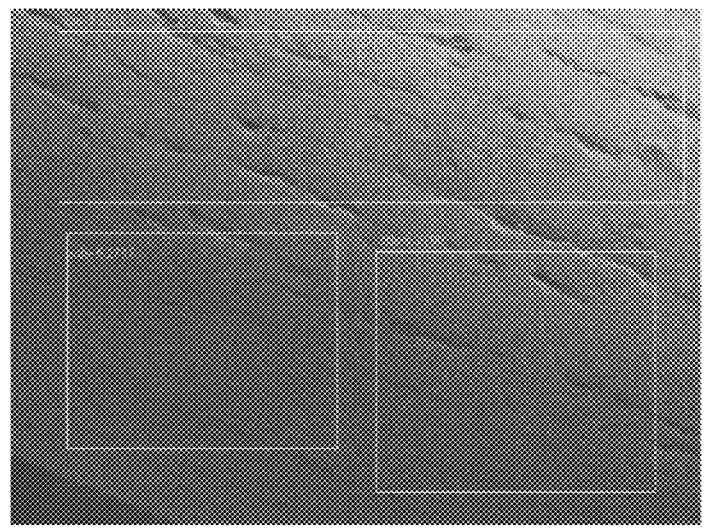
Figure 2C:
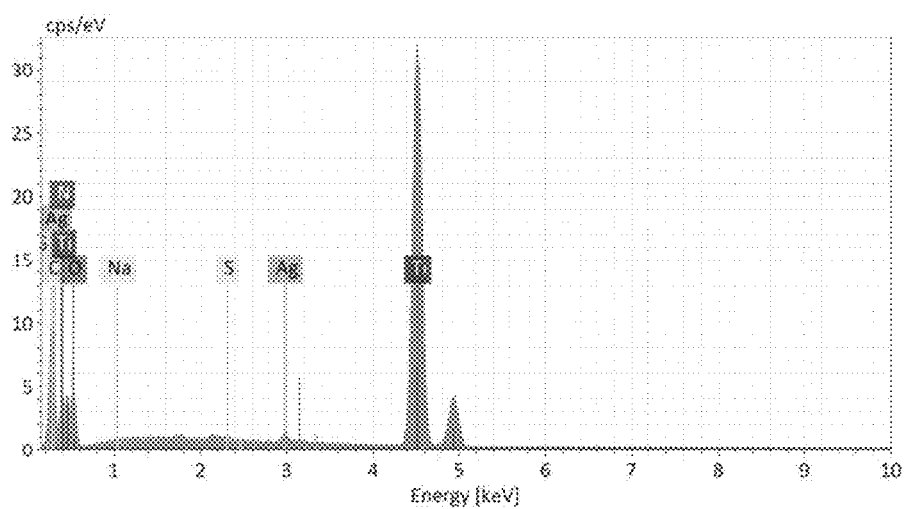

As shown in the field emission scanning electron microscopes FIGS. 1A, 1B and X-ray photoelectron spectrogram and data (FIGS. 2A-2C), the surface of pure titanium attached with the polydopamine film contained C, O, N and Ti, wherein C, O, and N were major components of the polydopamine and its precursor dopamine monomer ($C_8H_{11}NO_2$) (as shown in FIG. 2A). After the sulfadiazine reacted with the polydopamine film in an alkaline solution, the X-ray photoelectron spectrogram and data thereof exhibited elements such as C, O, N, S, Na (as shown in FIG. 2B), indicating that sodium sulfadiazine ($C_{10}H_9N_4NaO_2S$) was attached to the polydopamine film. The data in FIG. 2C contained elements such as C, O, N, S, N, Ag, and the like, indicating that silver sulfadiazine ($C_{10}H_9N_4AgO_2S$) was finally synthesized on the polydopamine film. This result was also supported by the morphology of the field emission scanning electron micrograph.

Figure 3A:
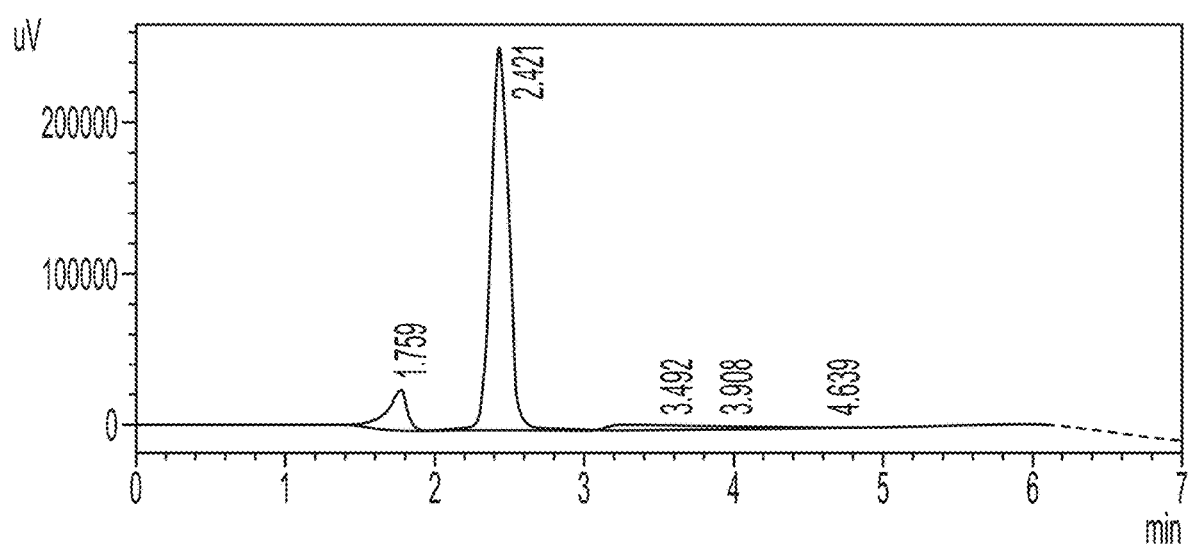
FIG. 3A is a high performance liquid chromatogram of a silver sulfadiazine control.
Figure 3B:
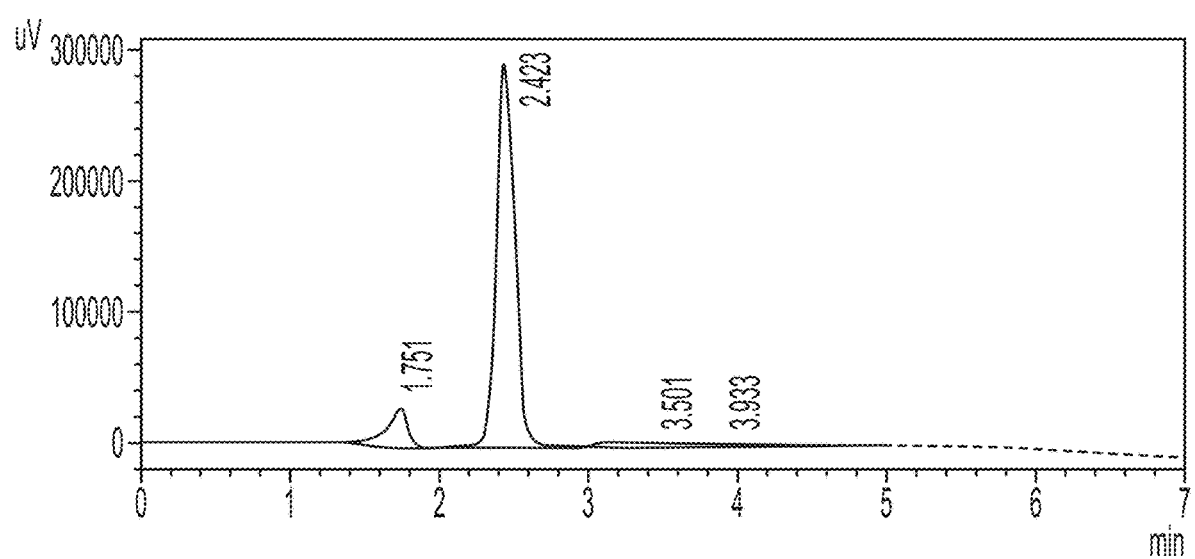
FIG. 3B is a high performance liquid chromatogram of silver sulfadiazine in-situ synthesized in Example 1.

The polydopamine film, polydopamine-sulfadiazine sodium complex and polydopamine-sulfadiazine silver complex attached to the surfaces of pure titanium were ground off physically and dissolved in 10% aqueous ammonia, respectively, and then the resulting samples were detected by high performance liquid chromatography and compared with the control. The retention time of polydopamine-sulfadiazine silver on the titanium surface in the high performance liquid chromatography was consistent with the retention time of the control sulfadiazine silver, which also illustrated that silver sulfadiazine was synthesized on polydopamine films. FIG. 3A was a chromatogram of a silver sulfadiazine control product, and FIG. 3B was a chromatogram of the silver sulfadiazine in-situ synthesized in Example 1. The chromatogram of the in-situ synthesized silver sulfadiazine was consistent with the chromatogram of the silver sulfadiazine control product, which illustrated that silver sulfadiazine was in-situ synthesized on polydopamine films.

The foregoing descriptions of specific exemplary embodiments of the present invention are for illustrative purposes. These descriptions are not intended to restrict the present invention to the precise forms disclosed, and it is clear that numerous changes and variations can be made in light of the above teachings. The purpose of selecting and describing exemplary embodiments is to explain the particular principles of the present invention and their practical applications, such that those skilled in the art are able to implement and utilize various different exemplary embodiments of the present invention and various different options and changes. The scope of the present invention is intended to be defined by the claims and their equivalents.

The invention claimed is:

1. A polydopamine film, characterized by being loaded with silver sulfadiazine under conditions of microwave irradiation,
wherein the polydopamine film loaded with silver sulfadiazine is free of a catalyst trifluoromethanesulfonic acid and a trifluoromethanesulfonic salt residue.

* * * * *